United States Patent
Reese et al.

(10) Patent No.: US 6,506,894 B1
(45) Date of Patent: Jan. 14, 2003

(54) SOLUTION PHASE SYNTHESIS OF OLIGONUCLEOTIDES

(75) Inventors: Colin Bernard Reese, London (GB); Quanlai Song, San Marcos, CA (US)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/485,606

(22) PCT Filed: Aug. 10, 1998

(86) PCT No.: PCT/GB98/02407

§ 371 (c)(1),
(2), (4) Date: Apr. 26, 2000

(87) PCT Pub. No.: WO99/09041

PCT Pub. Date: Feb. 25, 1999

(30) Foreign Application Priority Data

Aug. 13, 1997 (GB) .............................................. 9717158

(51) Int. Cl.⁷ ........................ C07H 21/00; C07H 21/02; C07H 21/04
(52) U.S. Cl. ...................... 536/25.3; 536/22.1; 536/23.1
(58) Field of Search ........................... 536/25.33, 27.21, 536/25.6, 26.1, 23.1, 22.1; 514/44; 435/6, 91.1

(56) References Cited

U.S. PATENT DOCUMENTS

| | | | |
|---|---|---|---|
| 3,546,185 A | | 12/1970 | Coran et al. ................ 260/79.5 |
| 5,149,798 A | * | 9/1992 | Agrawal et al. ............ 536/25.3 |
| 5,708,161 A | * | 1/1998 | Reese ....................... 536/25.33 |

FOREIGN PATENT DOCUMENTS

| | | |
|---|---|---|
| EP | 0 723 973 A1 | 7/1996 |
| WO | 94/15946 A | 7/1994 |
| WO | WO-9415946 A1 * | 7/1994 |

OTHER PUBLICATIONS

Muller et al, Tetrahedron Letters, 31:501–2, 1990.
Liu et al, J. Chem. Soc. Perkin Trans., 1:1685–94, 1995.
Andrus et al, Tetrahedron Letters 29:861–4, 1988.
Ozola et al, Tetrahedron Letters, 37:8621–4, 1996.
Froehler et al, Nucleic Acids, 14:5399–5407, 1986.
Dreef et al, Synlett., pp. 481–483 (Aug. 1990).
Brill W K–D: "Thioalkylation of Nucleoside–H–phosphonates and its Application to Solid Phase Synthesis of Oligonucleotides" Tetrahedron Letters, vol. 36, No. 5, Jan. 30, 1995, pp. 703–706 XP004028873 see p. 705; figure 3.
Sakatsume O. Et Al.: "Use of phosphonylating and coupling agents in the synthesis of oligodeoxyribonucleotides" Tetrahedron Letters, vol. 30, No. 46, 1989, pp. 6375–6378, XP002094935 see p.6376, syntheses of compounds 3 and 5, see p. 6377, reaction scheme.
Dreef C.E. Et Al.: "Phosphorylation of benzyl–protected sugar derivatives via 1–H–phosphonate intermediates: synthesis of DL–myo–inositol 1,4,5–tris–1–H–phosphonate" Recueil Des Travaux Chimiques Des Pays–Bas, vol. 106, 1987, pp. 512–513, XP002094936 see p. 513, scheme.
Shadid B.; Van Der Plas H.C.: "The synthesis of phosphor derivatives of ribosyl zeatin" Tetrahedron, vol. 46, No. 6, 1990, pp. 2179–2186, XP002094937 see p. 2180, structure see p. 2181.
Garegg P.J. Et Al.: "Nucleoside phosphonates: part 7. Studies on the oxidation of nucleoside phosphonate esters" Journal of the Chemical Society, Perkin Trans. I, 1987, pp. 1269–1274, XP002094938 see p. 1269, right–hand column see p. 1270, scheme 1.

\* cited by examiner

*Primary Examiner*—Sean McGarry
*Assistant Examiner*—Janet L Epps
(74) *Attorney, Agent, or Firm*—Pillsbury Winthrop LLP

(57) ABSTRACT

A process for the synthesis in solution phase of a phosphorothioate triester is provided. The process comprises the solution phase coupling of an H-phosphonate with an alcohol in the presence of a coupling agent to form an H-phosphonate diester. The H-phosphonate diester is oxidized in situ with a sulfur transfer agent to produce the phosphorothioate triester. Preferably, the H-phosphonate and alcohol are protected nucleosides or oligonucleotides. Oligonucleotide H-phosphonates which can be used in the formation of phosphorothioate triesters are also provided.

24 Claims, No Drawings

SOLUTION PHASE SYNTHESIS OF OLIGONUCLEOTIDES

This application is the national phase of the international application PCT/GB98/02407 filed Aug. 10, 1998 which designated the U.S.

The present invention provides a method of synthesising oligonucleotides and oligonucleotide phosphorothioates in solution based on H-phosphonate coupling and in situ sulfur transfer, carried out at low temperature. The invention further provides a process for the stepwise synthesis of oligonucleotides and oligonucleotide phosphorothioates in which one nucleoside residue is added at a time, and the block synthesis of oligonucleotides and oligonucleotide phosphorothioates in which two or more nucleotide residues are added at a time.

In the past 15 years or so, enormous progress has been made in the development of the synthesis of oligodeoxyribonucleotides (DNA sequences), oligoribonucleotides (RNA sequences) and their analogues 'Methods in Molecular Biology, Vol. 20, Protocol for Oligonucleotides and Analogs', Agrawal, S. Ed., Humana Press, Totowa, 1993. Much of the work has been carried out on a micromolar or even smaller scale, and automated solid phase synthesis involving monomeric phosphoramidite building blocks Beaucage, S. L.; Caruthers, M. H. *Tetrahedron Lett.*, 1981, 22, 1859–1862 has proved to be the most convenient approach. Indeed, high molecular weight DNA and relatively high molecular weight RNA sequences can now be prepared routinely with commercially available synthesisers. These synthetic oligonucleotides have met a number of crucial needs in biology and biotechnology.

Following Zamecnik and Stephenson's seminal discovery that a synthetic oligonucleotide could selectively inhibit gene expression in Rous sarcoma virus, (Zamecnik, P.; Stephenson, M. *Proc. Natl. Acad. Sci. USA* 1978, 75, 280–284), the idea that synthetic oligonucleotides or their analogues might well find application in chemotherapy has attracted a great deal of attention both in academic and industrial laboratories. For example, the possible use of oligonucleotides and their phosphorothioate analogues in chemotherapy has been highlighted in the report of Gura, T. Science, 1995, 270, 575–577. The so-called antisense and antigene approaches to chemotherapy (Oligonucleotides. Antisense Inhibitors of Gene Expression, Cohen. J. S., Ed., Macmillan, Basingstoke 1989 Moser, H. E.; Dervan, P. B. *Science* 1987, 238, 645–649), have profoundly affected the requirements for synthetic oligonucleotides. Whereas milligram quantities have generally sufficed for molecular biological purposes, gram to greater than 100 gram quantities are required for clinical trials. Several oligonucleotide analogues that are potential antisense drugs are now in advanced clinical trials. If, as seems likely in the very near future, one of these sequences becomes approved, say, for the treatment of AIDS or a form of cancer, kilogram or more probably multikilogram quantities of a specific sequence or sequences will be required.

In the past few years, a great deal of work has been carried out on the scaling-up of oligonucleotide synthesis. Virtually all of this work has involved building larger and larger synthesisers and the same phosphoramidite chemistry on a solid support. The applicant is unaware of any recent improvement in the methodology of the phosphotriester approach to oligonucleotide synthesis in solution, which makes it more suitable for large- and even moderate-scale synthetic work than solid phase synthesis.

The main advantages that solid phase has over solution synthesis are (i) that it is much faster, (ii) that coupling yields are generally higher, (iii) that it is easily automated and (iv) that it is completely flexible with respect to sequence. Thus solid phase synthesis is particularly useful if relatively small quantities of a large number of oligonucleotides sequences are required for, say, combinatorial purposes. However, if a particular sequence of moderate size has been identified and approved as a drug and kilogram quantities are required, speed and flexibility become relatively unimportant, and synthesis in solution is likely to be highly advantageous. Solution synthesis also has the advantage over solid phase synthesis in that block coupling (i.e. the addition of two or more nucleotide residues at a time) is more feasible and scaling-up to any level is unlikely to present a problem. It is much easier and certainly much cheaper to increase the size of a reaction vessel than it is to produce larger and larger automatic synthesisers.

In the past, oligonucleotide synthesis in solution has been carried out mainly by the conventional phosphotriester approach that was developed in the 1970s (Reese, C. B., *Tetrahedron* 1978, 34, 3143–3179; Kaplan, B. E.; Itakura, K. in 'Synthesis and Applications of DNA and RNA', Narang, S. A., Ed., Academic Press, Orlando, 1987, pp. 9–45). This approach can also be used in solid phase synthesis but coupling reactions are somewhat faster and coupling yields are somewhat greater when phosphoramidite monomers are used. This is why automated solid phase synthesis has been based largely on the use of phosphoramidite building blocks; it is perhaps also why workers requiring relatively large quantities of synthetic oligonucleotides have decided to attempt the scaling-up of phosphoramidite-based solid phase synthesis.

Three main methods, namely the phosphotriester (Reese, Tetrahedron, 1978), phosphoramidite (Beaucage, S. L. in *Methods in Molecular Biology*, Vol. 20, Agrawal, S., Ed., Humana Press, Totowa, 1993, pp 33–61) and H-phosphonate (Froehler, B. C. in *Methods in Molecular Biology*, Vol. 20, Agrawal, S., Ed., Humana Press, Totowa, 1993, pp 63–80; see also WO94/15946 and Dreef, C. E. in Rec. Trav. Chim. Pays-Bas, 1987, 106, p512) approaches have proved to be effective for the chemical synthesis of oligonucleotides. While the phosphotriester approach has been used most widely for synthesis in solution, the phosphoramidite and H-phosphonate approaches have been used almost exclusively in solid phase synthesis.

Two distinct synthetic strategies have been applied to the phosphotriester approach in solution.

Perhaps the most widely used strategy for the synthesis of oligodeoxyribonucleotides in solution involves a coupling reaction between a protected nucleoside or oligonucleotide 3'-(2-chlorophenyl)phosphate (Chattopadhyaya, J. B.; Reese, C. B. *Nucleic Acids Res.*, 1980, 8, 2039–2054) and a protected nucleoside or oligonucleotide with a free 5'-hydroxy function to give a phosphotriester. A coupling agent such as 1-(mesitylene-2-sulfonyl)-3-nitro-1,2,4-1H-triazole (MSNT) (Reese, C. B.; Titmas, R. C.; Yau, L. *Tetrahedron Lett.*, 1978, 2727–2730) is required. This strategy has also been used in the synthesis of phosphorothioate analogues. Coupling is then effected in the same way between a protected nucleoside or oligonucleotide 3'-S-(2-cyanoethyl or, for example, 4nitrobenzyl)phosphorothioate (Liu, X.; Reese, C. B. *J. Chem. Soc., Perkin Trans.* 1, 1995, 1685–1695) and a protected nucleoside or oligonucleotide with a free 5'-hydroxy function. The main disadvantages of this conventional phosphotriester approach are that some concomitant 5'-sulfonation of the second component occurs (Reese, C. B.; Zhang, P.-Z. *J. Chem. Soc., Perkin Trans.* 1, 1995, 2291–2301) and that coupling reactions generally proceed relatively slowly. The sulfonation side-reaction both leads to lower yields and impedes the purification of the desired products.

The second strategy for the synthesis of oligodeoxyribonucleotides in solution involves the use of a bifunctional reagent derived from an aryl (usually 2-chlorophenyl) phosphorodichloridate and two molecular equivalents of an additive such as 1-hydroxybenzotriazole (van der Marel, et al, *Tetrahedron Lett.*, 1981, 22, 3887–3890). A related bifunctional reagent, derived from 2,5-dichlorophenyl phosphorodichloridothioate (Scheme 1b), has similarly been used (Kemal, O et al, *J. Chem. Soc., Chem. Commun.*, 1983, 591–593) in the preparation of oligonucleotide phosphorothioates.

The main disadvantages of the second strategy result directly from the involvement of a bifunctional reagent. Thus the possibility exists of symmetrical coupling products being formed, and the presence of small quantities of moisture can lead to a significant diminution in coupling yields.

It is an objective of certain aspects of the present invention to provide a new coupling procedure for the synthesis of oligonucleotides in solution that in many embodiments (a) is extremely efficient and does not lead to side-reactions, (b) proceeds relatively rapidly, and (c) is equally suitable for the preparation of oligonucleotides, their phosphorothioate analogues and chimeric oligonucleotides containing both phosphodiester and phosphorothioate diester internucleotide linkages.

According to a first aspect of the present invention, there is provided a process for the preparation of a phosphorothioate triester which comprises the solution phase coupling of an H-phosphonate with an alcohol in the presence of a coupling agent thereby to form an H-phosphonate diester and, in situ, reacting the H-phosphonate diester with a sulfur transfer agent to produce a phosphorothioate triester.

The H-phosphonate employed in the process of the present invention is advantageously a protected nucleoside or oligonucleotide H-phosphonate, preferably comprising a 5' or a 3' H-phosphonate function, particularly preferably a 3' H-phosphonate function. Preferred nucleosides are 2'-deoxyribonucleosides and ribonucleosides; preferred oligonucleotides are oligodeoxyribonucleotides and oligoribonucleotides.

When the H-phosphonate building block is a protected deoxyribonucleoside, ribonucleoside, oligodeoxyribonucleotide or oligoribonucleotide derivative comprising a 3' H-phosphonate function, the 5' hydroxy function is advantageously protected by a suitable protecting group. Examples of such suitable protecting groups include acid labile protecting groups, particularly trityl and substituted trityl groups such as dimethoxytrityl and 9-phenylxanthen-9-yl groups; and base labile-protecting groups such as FMOC.

When the H-phosphonate building block is a protected deoxyribonucleoside, ribonucleoside, oligodeoxyribonucleotide or oligoribonucleotide derivative comprising a 5' H-phosphonate function, the 3' hydroxy function is advantageously protected by a suitable protecting group. Suitable protecting groups include those disclosed above for the protection of the 5' hydroxy functions of 3' H-phosphonate building blocks and acyl, such as levulinoyl and substituted levulinoyl, groups.

When the H-phosphonate is a protected ribonucleoside or a protected oligoribonucleotide, the 2'-hydroxy function is advantageously protected by a suitable protecting group, for example an acid-labile acetal protecting group, particularly 1-(2-fluorophenyl)-4-methoxypiperidine-4-yl (Fpmp); and trialkylsilyl groups, often tri($C_{1-4}$-alkyl)silyl groups such as a tertiary butyl dimethylsilyl group. Alternatively, the ribonucleoside or oligoribonucleotide may be a 2'-O-alkyl, 2'-O-alkoxyalkyl or 2'-O-alkenyl derivative, commonly a $C_{1-4}$ alkyl, $C_{1-4}$ alkoxy$C_{1-4}$alkyl or alkenyl derivative, in which case, the 2' position does not need further protection.

Other H-phosphonates that may be employed in the process according to the present invention are derived from other polyfunctional alcohols, especially alkyl alcohols, and preferably diols or triols. Examples of alkyl diols include ethane-1,2-diol, and low molecular weight poly(ethylene glycols), such as those having a molecular weight of up to 400. Examples of alkyl triols include glycerol and butane triols. Commonly, only a single H-phosphonate function will be present, the remaining hydroxy groups being protected by suitable protecting groups, such as those disclosed hereinabove for the protection at the 5' or 2' positions of ribonucleosides.

The alcohol employed in the process of the present invention is commonly a protected nucleoside or oligonucleotide comprising a free hydroxy group, preferably a free 3' or 5' hydroxy group, and particularly preferably a 5' hydroxy group.

When the alcohol is a protected nucleoside or a protected oligonucleotide, preferred nucleosides are deoxyribonucleosides and ribonucleosides and preferred oligonucleotides are oligodeoxyribonucleotides and oligoribonucleotides.

When the alcohol is a deoxyribonucleoside, ribonucleoside oligodeoxyribonucleotide or oligoribonucleotide derivative comprising a free 5'-hydroxy group, the 3'-hydroxy function is advantageously protected by a suitable protecting group. Examples of such protecting groups include acyl groups, commonly comprising up to 16 carbon atoms, such as those derived from gamma keto acids, such as levulinoyl groups and substituted levulinoyl groups. Substituted levulinoyl groups include particularly 5-halo-levulinoyl, such as 5,5,5-trifluorolevulinoyl and benzoylpropionyl groups. Other such protecting groups include fatty alkanoyl groups, including particularly linear or branched $C_{6-16}$ alkanoyl groups, such as lauroyl groups; benzoyl and substituted benzoyl groups, such as alkyl, commonly $C_{1-4}$ alkyl-, and halo, commonly chloro or fluoro, substituted benzoyl groups; and silyl ethers, such as alkyl, commonly $C_{1-4}$ alkyl, and aryl, commonly phenyl, silyl ethers, particularly tertiary butyl dimethyl silyl and tertiary butyl diphenyl silyl groups.

When the alcohol is a protected deoxyribonucleoside, ribonucleoside, oligodeoxyribonucleotides or oligoribonucleotide comprising a free 3'-hydroxy group, the 5'-hydroxy function is advantageously protected by a suitable protecting group. Suitable protecting groups are those disclosed above for the protection of the 5' hydroxy group of deoxyribonucleosides, ribonucleosides, oligodeoxyribonucleotides and oligoribonucleotide 3' H phosphonates.

When the alcohol is a ribonucleoside or an oligoribonucleotide, the 2'-hydroxy function is advantageously protected by a suitable protecting group, such as an acetal, particularly 1-(2-fluorophenyl)4-methoxypiperidine4-yl (Fpmp); and trialkylsilyl groups, often tri($C_{1-4}$-alkyl)silyl groups such as a tertiary butyl dimethyl silyl group. Alternatively, the ribonucleoside or oligoribonucleotide may be a 2'-O-alkyl, 2'-O-alkoxyalkyl or 2'-O-alkenyl derivative, commonly a $C_{1-4}$ alkyl, $C_{1-4}$ alkoxy$C_{1-4}$alkyl or alkenyl derivative, in which case, the 2' position does not need further protection.

Other alcohols that may be employed in the process according to the present invention are non-saccharide polyols, especially alkyl polyols, and preferably diols or triols. Examples of alkyl diols include ethane-1,2-diol, and low molecular weight poly(ethylene glycols), such as those having a molecular weight of up to 400. Examples of alkyl triols include glycerol and butane triols. Commonly, only a single free hydroxy group will be present, the remaining hydroxy groups being protected by suitable protecting groups, such as those disclosed hereinabove for the protection at the 5' or 2' positions of ribonucleosides. However, more than one free hydroxy group may be present if it is desired to perform identical couplings on more than one hydroxy group.

When the H-phosphonate and the alcohol are both protected nucleosides or oligonucleotides, the invention provides an improved method for the stepwise and block synthesis in solution of oligodeoxyribonucleotides, oligoribonucleotides and analogues thereof, based on H-phosphonate coupling reactions. According to one preferred aspect of the present invention, protected nucleosides or oligonucleotides with a 3'-terminal H-phosphonate function and protected nucleosides or oligonucleotides with a 5'-terminal hydroxy function are coupled in the presence of a suitable coupling agent to form a protected dinucleoside or oligonucleotide H-phosphonate intermediate, wherein said intermediates undergo sulfur-transfer in situ in the presence of a suitable sulfur-transfer agent.

In addition to the presence of hydroxy protecting groups, bases present in nucleosides/nucleotides employed in present invention are also preferably protected where necessary by suitable protecting groups. Protecting groups employed are those known in the art for protecting such bases. For example, A and/or C can be protected by benzoyl, including substituted benzoyl, for example alkyl- or alkoxy-, often $C_{1-4}$ alkyl- or $C_{1-4}$ alkoxy-, benzoyl; pivaloyl; and amidine, particularly dialkylaminomethylene, preferably di($C_{1-4}$-alkyl)aminomethylene such as dimethyl or dibutyl aminomethylene. G may be protected by a phenyl group, including substituted phenyl, for example 2,5-dichlorophenyl and also by an isobutyryl group. T and U generally do not require protection, but in certain embodiments may advantageously be protected, for example at O4 by a phenyl group, including substituted phenyl, for example 2,4-dimethylphenyl or at N3 by a pivaloyloxymethyl, benzoyl, alkyl or alkoxy substituted benzoyl, such as $C_{1-4}$ alkyl- or $C_{1-4}$ alkoxybenzoyl.

When the alcohol and/or H-phosphonate is a protected nucleoside or oligonucleotide having protected hydroxy groups, one of these protecting groups may be removed after carrying out the process of the first invention. Commonly, the protecting group removed is that on the 3'-hydroxy function. After the protecting group has been removed, the oligonucleotide thus formed may be converted into an H-phosphonate and may then proceed through further stepwise or block coupling and sulfur transfers according to the process of the present invention in the synthesis of a desired oligonucleotide sequence. The method may then proceed with steps to remove the protecting groups from the internucleotide linkages, the 3' and the 5'-hydroxy groups and from the bases. Similar methodology may be applied to coupling 5' H-phosphonates, wherein the protecting group removed is that on the 5' hydroxy function.

In a particularly preferred embodiment, the invention provides a method comprising the coupling of a 5'-O-(4,4'-dimethoxytrityl)-2'-deoxyribonucleoside 3'-H-phosphonate or a protected oligodeoxyribonucleotide 3'-H-phosphonate and a component with a free 5'-hydroxy function in the presence of a suitable coupling agent and subsequent in situ sulfur transfer in the presence of a suitable sulfur-transfer agent.

In the process of the present invention, any suitable coupling agents and sulfur-transfer agents available in the prior art may be used.

Examples of suitable coupling agents include alkyl and aryl acid chlorides, alkane and arene sulfonyl chlorides, alkyl and aryl chloroformates, alkyl and aryl chlorosulfites and alkyl and aryl phosphorochloridates.

Examples of suitable alkyl acid chlorides which may be employed include $C_2$ to $C_7$ alkanoyl chlorides, particularly pivaloyl chloride. Examples of aryl acid chlorides which may be employed include substituted and unsubstituted benzoyl chlorides, such as $C_{1-4}$ alkoxy, halo, particularly fluoro, chloro and bromo, and $C_{1-4}$ alkyl, substituted benzoyl chlorides. When substituted, from 1 to 3 substituents are often present, particularly in the case of alkyl and halo substituents.

Examples of suitable alkanesulfonyl chlorides which may be employed include $C_2$ to $C_7$ alkanesulfonyl chlorides. Examples of arenesulfonyl chlorides which may be employed include substituted and unsubstituted benzenesulfonyl chlorides, such as $C_{1-4}$ alkoxy, halo, particularly fluoro, chloro and bromo, and $C_{1-4}$ alkyl, substituted benzenesulfonyl chlorides. When substituted, from 1 to 3 substituents are often present, particularly in the case of alkyl and halo substituents.

Examples of suitable alkyl chloroformates which may be employed include $C_2$ to $C_7$ alkyl chloroformates. Examples of aryl chloroformates which may be employed include substituted and unsubstituted phenyl chloroformates, such as $C_{1-4}$ alkoxy, halo, particularly fluoro, chloro and bromo, and $C_{1-4}$ alkyl, substituted phenyl chloroformates. When substituted, from 1 to 3 substituents are often present, particularly in the case of alkyl and halo substituents.

Examples of suitable alkyl chlorosulfites which may be employed include $C_2$ to $C_7$ alkyl chlorosulfites. Examples of aryl chlorosulfites which may be employed include substituted and unsubstituted phenyl chlorosulfites, such as $C_{1-4}$ alkoxy, halo, particularly fluoro, chloro and bromo, and $C_{1-4}$ alkyl, substituted phenyl chlorosulfites. When substituted, from 1 to 3 substituents are often present, particularly in the case of alkyl and halo substituents.

Examples of suitable alkyl phosphorochloridates which may be employed include di($C_1$ to $C_6$ alkyl) phosphorochloridates. Examples of aryl phosphorochloridates which may be employed include substituted and unsubstituted diphenyl phosphorochloridates, such as $C_{1-4}$ alkoxy, halo, particularly fluoro, chloro and bromo, and $C_{1-4}$ alkyl, substituted diphenyl phosphorochloridates. When substituted, from 1 to 3 substituents are often present, particularly in the case of alkyl and halo substituents.

Further coupling agents that may be employed are the chloro-, bromo- and (benzotriazo-1-yloxy)-phosphonium and carbonium compounds disclosed by Wada et al, in J.A.C.S. 1997, 119, pp 12710–12721 (incorporated herein by reference).

Preferred coupling agents are diaryl phosphorochloridates, particularly those having the formula (ArO)$_2$POCl wherein Ar is preferably phenyl, 2-chlorophenyl, 2,4,6-trichlorophenyl or 2,4,6-tribromophenyl.

The nature of the sulfur-transfer agent will depend on whether an oligonucleotide, a phosphorothioate analogue or a mixed oligonucleotide/oligonucleotide phosphorothioate is required. Sulfur transfer agents employed in the process of the present invention often have the general chemical formula:

$$L-S-A$$

wherein L represents a leaving group, and A represents an aryl group, a methyl or a substituted alkyl group or an alkenyl group. Commonly the leaving group is selected so as to comprise a nitrogen-sulfur bond. Examples of suitable leaving groups include morpholines such as morpholine-3, 5-dione; imides such as phthalimides, succinimides and maleimides; indazoles, particularly indazoles with electron-withdrawing substituents such as 4-nitroindazoles; and triazoles.

Where a standard phosphodiester linkage is required in the final product, the sulfur transfer agent, the moiety A represents an aryl group, such as a phenyl or naphthyl group. Examples of suitable aryl groups include substituted and unsubstituted phenyl groups, particularly halophenyl and alkylphenyl groups, especially 4-halophenyl and 4-alkylphenyl, commonly 4-($C_{1-4}$ alkyl)phenyl groups, most preferably 4-chlorophenyl and p-tolyl groups. An example of a suitable class of standard phosphodiester-directing sulfur-transfer agent is an N-(arylsulfanyl)phthalimide (succinimide or other imide may also be used).

Where a phosphorothioate diester linkage is required in the final product, the moiety A represents a methyl, substituted alkyl or alkenyl group. Examples of suitable substituted alkyl groups include substituted methyl groups, particularly benzyl and substituted benzyl groups, such as alkyl-, commonly $C_{1-4}$alkyl- and halo-, commonly chloro-, substituted benzyl groups, and substituted ethyl groups, especially ethyl groups substituted at the 2-position with an electron-withdrawing substituent such as 2-(4-nitrophenyl)ethyl and 2-cyanoethyl groups. Examples of suitable alkenyl groups are allyl and crotyl. Examples of a suitable class of phosphorothioate-directing sulfur-transfer agents are, for example, (2-cyanoethyl)sulfanyl derivatives such as 4-[(2-cyanoethyl)-sulfanyl]morpholine-3,5-dione or a corresponding reagent such as 3-(phthalimidosulfanyl)propanonitrile.

A suitable temperature for carrying out the coupling reaction and sulfur transfer is in the range of approximately–55° C. to room temperature (commonly in the range of from 10 to 30° C., for example approximately 20° C.), and preferably from –40° C. to 0° C.

Organic solvents which can be employed in the process of the present invention include haloalkanes, particularly dichloromethane, esters, particularly alkyl esters such as ethyl acetate, and methyl or ethyl propionate, and basic, nucleophilic solvents such as pyridine. Preferred solvents for the coupling and sulfur transfer steps are pyridine, dichloromethane and mixtures thereof.

The mole ratio of H-phosphonate to alcohol in the process of the present invention is often selected to be in the range of from about 0.9:1 to 3:1, commonly from about 1:1 to about 2:1, and preferably from about 1.1:1 to about 1.5:1, such as about 1.2:1. However, where couplings on more than one free hydroxyl are taking place at the same time, the mole ratios will be increased proportionately. The mole ratio of coupling agent to alcohol is often selected to be in the range of from about 1:1 to about 10:1, commonly from about 1.5:1 to about 5:1 and preferably from about 2:1 to about 3:1. The mole ratio of sulfur transfer agent to alcohol is often selected to be in the range of from about 1:1 to about 10:1, commonly from about 1.5:1 to about 5:1 and preferably from about 2:1 to about 3:1.

In the process of the present invention, the H-phosphonate and the alcohol can be pre-mixed in solution, and the coupling agent added to this mixture. Alternatively, the H-phosphonate and the coupling agent can be pre-mixed, often in solution and then added to a solution of the alcohol, or the alcohol and the coupling agent may be mixed, commonly in solution, and then added to a solution of the H-phosphonate. In certain embodiments, the H-phosphonate, optionally in the form of a solution, can be added to a solution comprising a mixture of the alcohol and the coupling agent. After the coupling reaction is substantially complete, the sulfur transfer agent is then added to the solution the H-phosphonate diester produced in the coupling reaction. Reagent additions commonly take place continuously or incrementally over an addition period.

In the process of the present invention, it is possible to prepare oligonucleotides containing both phosphodiester and phosphorothioate diester internucleotide linkages in the same molecule by selection of appropriate sulfur transfer agents, particularly when the process is carried out in a stepwise manner.

As stated previously, the method of the invention can be used in the synthesis of RNA, 2'-O-alkyl-RNA, 2'-O-alkoxyalkyl-RNA and 2'-O-alkenyl-RNA sequences. 2'-O (Fpmp)-5'-O-(4,4-dimethoxytrityl)-ribonucleoside 3'-H-phosphonates 1 and 2'-O-(alkyl, alkoxyalkyl or alkenyl)-5'-O-(4,4-dimethoxytrityl)-ribonucleoside 3'-H-phosphonates 2a–c may be prepared, for example, from the corresponding nucleoside building blocks, ammonium p-cresyl H-phosphonate and pivaloyl chloride.

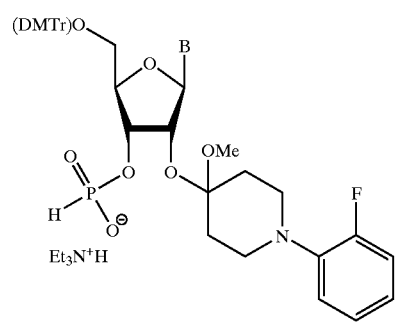

1

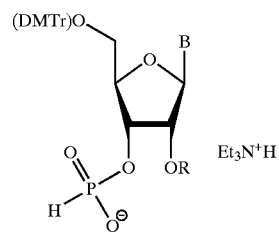

2 a : R = Me
b : R = CH$_2$ = CHCH$_2$
c : R = MeOCH$_2$CH$_2$

The same protocols are used as in the synthesis of DNA and DNA phosphorothioate sequences (Schemes 2–4). Following the standard unblocking procedure (Scheme 2, steps v and vi), the Fpmp protecting groups are removed under mild conditions of acidic hydrolysis that lead to no detectable cleavage or migration of the internucleotide linkages (Capaldi, D. C.; Reese, C. B. *Nucleic Acids Res.* 1994, 22, 2209–2216). For chemotherapeutically useful ribozyme sequences, relatively large scale RNA synthesis in solution is a matter of considerable practical importance. The incorporation of 2'-O-alkyl, 2'-O-substituted alkyl and 2'-O-alkenyl [especially 2'-O-methyl, 2'-O-allyl and 2'-O-(2-methoxyethyl)]-ribonucleosides (Sproat, B. S. in 'Methods in Molecular Biology, Vol. 20. Protocols for Oligonucleotides and Analogs', Agrawal, S., Ed., Humana Press, Totowa, 1993) into oligonucleotides is currently a matter of much importance as these modifications confer both resistance to nuclease digestion and good hybridisation properties on the resulting oligomers.

The sulfur transfer step is carried out on the product of the H-phosphonate coupling in situ, ie without separation and purification of the intermediate produced by the coupling reaction. Preferably, the sulfur transfer agent is added to the stirred mixture resulting from the coupling reaction.

In addition to the fact that it is carried out in homogenous solution, the present coupling procedure differs from that followed in the H-phosphonate approach to solid phase synthesis (Froehler et al., Methods in Molecular Biology, 1993) in at least two other important respects. First, it may be carried out at a very low temperature. Side reactions which can accompany H-phosphonate coupling (Kuyl-Yeheskiely et al, *Rec. Trav. Chim.*, 1986, 105, 505–506) can thereby be avoided even when di-(2-chlorophenyl)phosphorodichloridate rather than pivaloyl chloride (Froehler, B. C.; Matteucci, M. D. *Tetrahedron Lett.*, 1986, 27, 469–472) is used as the coupling reagent. Secondly, sulfur transfer is carried out after each coupling step rather than just once following the assembly of the whole oligomer sequence.

Protecting groups can be removed using methods known in the art for the particular protecting group and function. For example, transient protecting groups, particularly gamma keto acids such as levulinoyl-type protecting groups, can be removed by treatment with hydrazine, for example, buffered hydrazine, such as the treatment with hydrazine under very mild conditions disclosed by van Boom. J. H.; Burgers, P. M. J. *Tetrahedron Lett.*, 1976, 4875–4878. The resulting partially-protected oligonucleotides with free 3'-hydroxy functions may then be converted into the corresponding H-phosphonates which are intermediates which can be employed for the block synthesis of oligonucleotides and their phosphorothioate analogues.

When deprotecting the desired product once this has been produced, protecting groups on the phosphorus which produce phosphorothioate triester linkages are commonly removed first. For example, a cyanoethyl group can be removed by treatment with a strongly basic amine such as DABCO, 1,5-diazabicylo[4.3.0]non-5-ene (DBN), 1,8-diazabicyclo[5.4.0]undec-7-ene (DBU) or triethylamine.

Phenyl and substituted phenyl groups on the phosphorothioate internucleotide linkages and on the base residues can be removed by oximate treatment, for example with the conjugate base of an aldoxime, preferably that of E-2-nitrobenzaldoxime or pyridine-2-carboxaldoxime (Reese et al, Nucleic Acids Res. 1981). Kamimura, T. et al in *J. Am. Chem. Soc.*, 1984, 106 4552–4557 and Sekine, M. Et al, *Tetrahedron*, 1985, 41, 5279–5288 in an approach to oligonucleotide,synthesis by the phosphotriester approach in solution, based on S-phenyl phosphorothioate intermediates; and van Boom and his co-workers in an approach to oligonucleotide synthesis, based on S-(4-methylphenyl) phosphorothioate intermediates (Wreesman, C. T. J. Et al, *Tetrahedron Lett.*, 1985, 26, 933–936) have all demonstrated that unblocking S-phenylphosphorothioates with oximate ions (using the method of Reese et al., 1978; Reese, C. B,; Zard, L. *Nucleic Acids Res.*, 1981, 9, 4611–4626) led to natural phosphodiester internucleotide linkages. In the present invention, the unblocking of S-(4-chlorophenyl)-protected phosphorothioates with the conjugate base of E-2-nitrobenzaldoxime proceeds smoothly and with no detectable internucleotide cleavage.

Other base protecting groups, for example benzoyl, pivaloyl and amidine groups can be removed by treatment with concentrated aqueous ammonia.

Trityl groups present can be removed by treatment with acid. With regard to the overall unblocking strategy in oligodeoxyribonucleotide synthesis, another important consideration of the present invention, is that the removal of trityl, often a 5'-terminal DMTr, protecting group ('detritylation') should proceed without concomitant depurination, especially of any 6-N-acyl-2'-deoxyadenosine residues. According to an embodiment of the invention, the present inventors have found that such depurination, which perhaps is difficult completely to avoid in solid phase synthesis, can be totally suppressed by effecting 'detritylation' with a dilute solution of hydrogen chloride at low temperature, particularly ca. 0.45 M hydrogen chloride in dioxane—dichloromethane (1:8 v/v) solution at–50° C. Under these reaction conditions, 'detritylation' can be completed rapidly, and in certain cases after 5 minutes or less. For example, when 6-N-benzoyl-5'-O-(4,4'-dimethoxytrityl)-2'-deoxyadenosine was treated with hydrogen chloride in dioxane—dichloromethane under such conditions, 'detritylation' was complete after 2 min, but no depurination was detected even after 4 hours.

Silyl protecting groups may be removed by fluoride treatment, for example with a solution of a tetraalkyl ammonium fluoride salt such as tetrabutyl ammonium fluoride.

Fpmp protecting groups may be removed by acidic hydrolysis under mild conditions.

This new approach to the synthesis of oligonucleotides in solution is suitable for the preparation of sequences with (a) solely phosphodiester, (b) solely phosphorothioate diester and (c) a combination of both phosphodiester and phosphorothioate diester internucleotide linkages.

The invention also relates to the development of block coupling (as illustrated for example in Scheme 4b). In this respect, the examples provide an illustration of the synthesis of d[Tp(s)Tp(s)Gp(s)Gp(s)Gp(s)Gp(s)Tp(s)T] (ISIS 5320 Ravikuma, V. T.; Cherovallath, Z. S. *Nucleosides & Nucleosides* 1996, 15, 1149–1155), an octadeoxyribonucleoside heptaphosphorothioate, from tetramer blocks. This oligonucleotide analogue has properties as an anti-HIV agent. Other proposed block synthesis targets include sequences with therapeutic effects, for example, inhibitors of human thrombin and anti-HIV agents. The method of the invention furthermore can be used in the synthesis of larger sequences.

It will be apparent that when the process of the present invention is applied to block synthesis, a number of alternative strategies are available in terms of the route to the desired product. These will depend on the nature of the desired product. For example, an octamer may be prepared by the preparation of dimers, coupled to produce tetramers, which are then coupled to produce the desired octamer. Alternatively, a dimer and a trimer may be coupled to produce a pentamer, which can be coupled with a further trimer to produce the desired octamer. The choice of strategy is at the discretion of the user. However, the common feature of such block coupling is that an oligomer H-phosphonate comprising two or more units is coupled with an oligomer alcohol also comprising two or more units. Most commonly oligonucleotide 3'-H-phosphonates are coupled with oligonucleotides having free 5'-hydroxy functions.

The process of the present invention can also be employed to prepare cyclic oligonucleotides, especially cyclic oligodeoxyribonucleotides and cyclic ribonucleotides. In the preparation of cyclic oligonucleotides, an oligonucleotides comprising an H-phosphonate function, often a 3' or 5' H-phosphonate is prepared, and a free hydroxy function is introduced by appropriate deprotection. The position of the free hydroxy function is usually selected to correspond to the H-phosphonate, for example a 5' hydroxy function would be coupled with a 3' H-phosphonate, and a 3' hydroxy function would be coupled with a 5' H-phosphonate. The hydroxy and the H-phosphonate functions can then be coupled intramolecularly in solution in the presence of a coupling agent and this reaction is followed by in situ sulfur transfer.

According to a further aspect of the present invention, there is provided novel oligomer H-phosphonates having the general chemical formula:

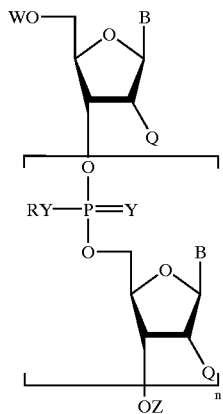

wherein
each B independently is a base selected from A, G, T, C or U;
each Q independently is H or OR' wherein R' is alkyl, substituted alkyl, alkenyl or a protecting group;
each R independently is an aryl, methyl, substituted alkyl or alkenyl group;
W is H, a protecting group or an H-phosphonate group of formula

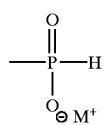

in which
$M^+$ is a monovalent cation;
each X independently represent O or S;
each Y independently represents O or S;
Z is H, a protecting group or an H-phosphonate group of formula

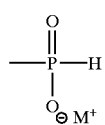

in which
$M^+$ is a monovalent cation; and
n is an integer and is at least 2;
provided that when W is H or a protecting group, that Z is an H-phosphonate group, and that when Z is H or a protecting group, that W is an H-phosphonate group.

Also provided are novel oligomer H-phosphonates having the general chemical formula:

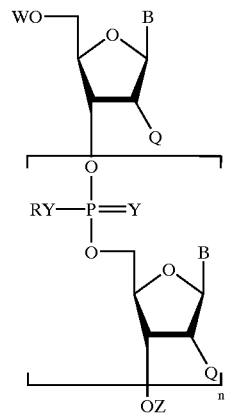

wherein
each B independently is a base selected from A, G, T, C or U;
each Q independently is H or OR' wherein R' is alkyl, substituted alkyl, alkenyl or a protecting group;
each R independently is an aryl, methyl, substituted alkyl or alkenyl group;
W is H, a protecting group or an H-phosphonate group of formula

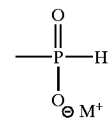

in which
$M^+$ is a monovalent cation;
each X independently represent O or S;
each Y represents S;
Z is H, a protecting group or an H-phosphonate group of formula

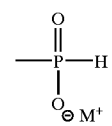

in which
$M^+$ is a monovalent cation; and
n is a positive integer;
provided that when W is H or a protecting group, that Z is an H-phosphonate group, and that when Z is H or a protecting group, that W is an H-phosphonate group.

Preferably, only one of W or Z is an H-phosphonate group, commonly only Z being an H-phosphonate group.

When W or Z represents a protecting group, the protecting group may be one of those disclosed above for protecting the 3' or 5' positions respectively. When W is a protecting group, the protecting group is a trityl group, particularly a dimethoxytrityl group. When Z is a protecting group, the protecting group is a trityl group, particularly a dimethoxytrityl group, or an acyl, preferably a levulinoyl group.

The bases A, G and C represented by B are preferably protected, and bases T and U may be protected. Suitable protecting groups include those described hereinabove for the protection of bases in the process according to the first aspect of the present invention.

When Q represents a group of OR', and R' is alkenyl, the alkenyl group is often a $C_{1-4}$ alkenyl group, especially allyl or crotyl group. When R' represents alkyl, the alkyl is preferably a $C_{1-4}$ alkyl group. When R' represents substituted alkyl, the substituted alkyl group includes alkoxyalkyl groups, especially $C_{1-4}$ alkyoxy$C_{1-4}$ alkyl groups such as methoxyethyl groups. When R' represents a protecting group, the protecting group is commonly an acid-labile acetal protecting group, particularly 1-(2-fluorophenyl)4-methoxypiperidine4-yl (Fpmp) or a trialkylsilyl groups, often a tri($C_{1-4}$-alkyl)silyl group such as a tertiary butyl dimethylsilyl group.

Preferably, X represents O.

In many embodiments, Y represents S and each R represents the methyl, substituted alkyl, alkenyl or aryl group remaining from the sulfur transfer agent(s) employed in the process of the present invention. Preferably, each R independently represents a methyl group; a substituted methyl group, particularly a benzyl or substituted benzyl group, such as an alkyl-, commonly $C_{1-4}$alkyl- or halo-, commonly chloro-, substituted benzyl group; a substituted ethyl group, especially an ethyl group substituted at the 2-position with an electron-withdrawing substituent such as a 2-(4-nitrophenyl)ethyl or a 2-cyanoethyl group; a $C_{1-4}$ alkenyl group, preferably an allyl and crotyl group; or a substituted or unsubstituted phenyl group, particularly a halophenyl or alkylphenyl group, especially 4-halophenyl group or a 4-alkylphenyl, commonly a 4-($C_{1-4}$ alkyl)phenyl group, and most preferably a 4-chlorophenyl or a p-tolyl group.

$M^+$ preferably represents a trialkyl ammonium ion, such as a tri($C_{1-4}$alkylammonium) ion, and preferably a triethylammonium ion.

n may be 1 up to any number depending on the oligonucleotide which is intended to be synthesised, particularly up to about 20. Preferably n is 1 to 16, and especially 1 to 9. H-phosphonate wherein n represents 1, 2 or 3 can be employed when it is desired to add small blocks of nucleotide, with correspondingly larger values of n, for example 5, 6 or 7 or more being employed if larger blocks of oligonucleotide are desired to be coupled.

The H-phosphonates according to the present invention are commonly in the form of solutions, preferably those employed in the process of the first aspect of the present invention.

These H-phosphonates are also useful intermediates in the block synthesis of oligonucleotides and oligonucleotide phosphorothioates. As indicated above, block coupling is much more feasible in solution phase than in solid phase synthesis.

The oligonucleotide H-phosphonates can be prepared using general methods known in the art for the synthesis of nucleoside H-phosphonates. Accordingly, in a further aspect of the present invention, there is provided a process for the production of an oligonucleotide H-phosphonate wherein an oligonucleotide comprising a free hydroxy function, preferably a 3' or 5' hydroxy function, is reacted with an alkyl or aryl H-phosphonate salt in the presence of an activator.

Preferably, the oligonucleotide is a protected oligonucleotide, and most preferably a protected oligodeoxynucleotide or a protected oligoribonucleotide. The H-phosphonate salt is often an ammonium salt, including alkyl, aryl and mixed alkyl and aryl ammonium salts. Preferably, the ammonium salt is an $(NH_4)^+$ or a tri($C_{1-4}$alkyl) ammonium salt. Examples of alkyl groups which may be present in the H-phosphonate are $C_{1-4}$ alkyl, especially $C_{2-4}$ alkyl, groups substituted with strongly electron withdrawing groups, particularly halo, and preferably fluoro groups, such as 2,2,2-trifluoroethyl and 1,1,1,3,3,3-hexafluoropropan-2-yl groups. Examples of aryl groups which may be present include phenyl and substituted phenyl, particularly alkylphenyl, commonly $C_{1-4}$ alkylphenyl and halophenyl, commonly chlorophenyl groups. Preferably, a substituted phenyl group is a 4-substituted phenyl group. Particularly preferred H-phosphonates are ammonium and triethylammonium p-cresyl H-phosphonates. Activators which may be employed include those compounds disclosed herein for use as coupling agents, and particularly diaryl phosphorochloridates and alkyl and cycloalkyl acid chlorides, such as 1-adamantanecarbonyl chloride, and preferably pivaloyl chloride. The production of H-phosphonates preferably takes place in the presence of a solvent, often those solvents disclosed for use in the process of the first aspect of the present invention, preferably pyridine, dichloromethane and mixtures thereof.

One advantage of the present invention for the synthesis of solely phosphorothioate diesters is that, provided care is taken to avoid desulfurisation during the unblocking steps [particularly during heating with aqueous ammonia (for example Scheme 3, step viii(a))], the synthesis of oligonucleotide phosphorothioates should not lead to products that are contaminated with standard phosphodiester internucleotide linkages. In the case of solid phase oligonucleotide phosphorothioate synthesis, incomplete sulfur transfer in each synthetic cycle usually leads to a residual phosphodiester contamination (Zon, G.; Stec, W. J. in 'Oligonucleotides and Analogs. A Practical Approach', Eckstein, F., Ed., IRL Press, Oxford, 1991, pp. 87–108).

The solution synthesis as proposed by the present invention has another enormous advantage over solid-phase synthesis in that the possibility exists of controlling the selectivity of reactions by working at low or even at very low temperatures. This advantage extends to the detritylation step (Scheme 3, step i) which can proceed rapidly and quantitatively below 0° C. without detectable depurination. After the detritylation step, a relatively quick and efficient purification can be effected by what has previously been described as the 'filtration' approach (Chaudhuri, B,; Reese, C. B.; Weclawek, K. *Tetrahedron Lett.* 1984, 25, 4037–4040). This depends on the fact that phosphotriester (and phosphorothioate triester) intermediates, but not any remaining detritylated charged monomers, are very rapidly eluted from short columns of silica gel by THF-pyridine mixtures.

The method according to the invention will now be illustrated with reference to the following examples which are not intended to be limiting:

In the Examples, it should be noted, that where nucleoside residues and internucleotide linkages are italicised, this indicates that they are protected in some way. In the present context, A, C, G, and T represent 2'-deoxyadenosine protected on N-6 with a benzoyl group, 2'-deoxycytidine protected on N-4 with a benzoyl group, 2'-deoxyguanosine protected on N-2 and on O-6 with isobutyryl and 2,5-dichlorophenyl groups and unprotected thymine. For example, as indicated in scheme 3, p(s) and p(s') represent S-(2-cyanoethyl) and S-(4-chlorophenyl)phosphorothioates, respectively, and p(H), which is not protected and therefore not italicised, represents an H-phosphonate monoester if it is placed at the end of a sequence or attached to a monomer but otherwise it represents an H-phosphonate diester.

EXAMPLES

Reaction Scheme for Preparation of Dinucleoside Phosphates

With particular reference to the preparation of dinucleoside phosphates, Scheme 2 describes in more detail the method of the invention for the preparation of oligodeoxyribonucleotides and the phosphorothioate analogues thereof.

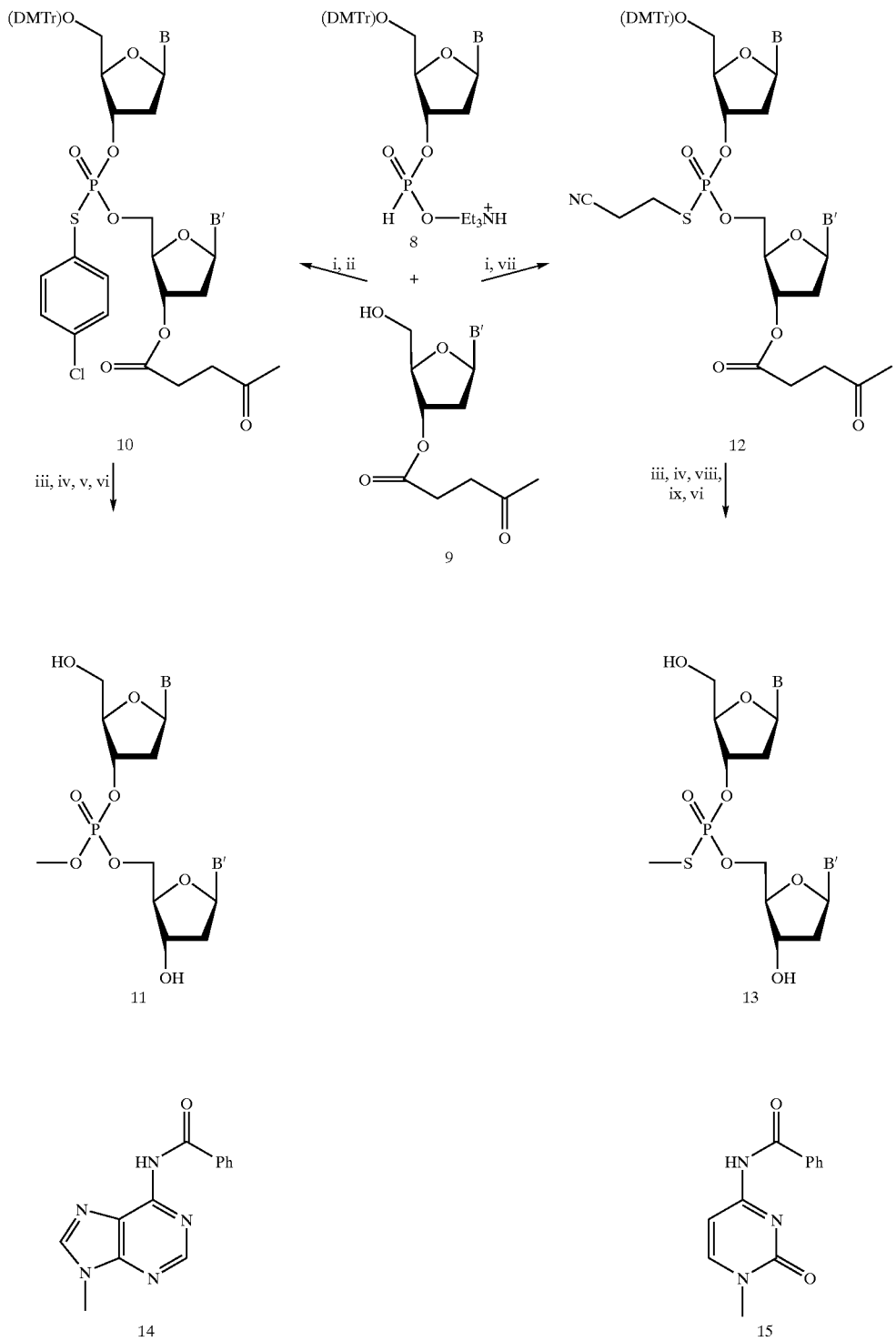

-continued

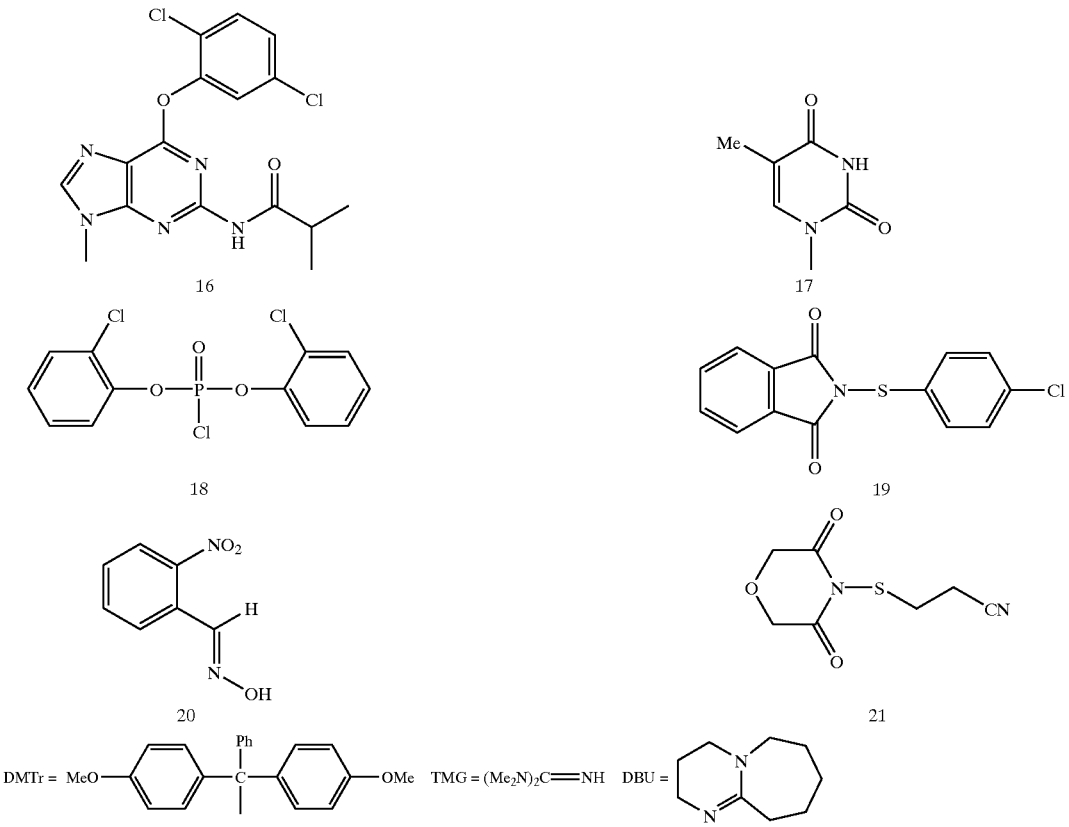

Scheme 2

Reagents and conditions:

(i) 18, C$_5$H$_5$N, CH$_2$Cl$_2$, −40° C., 5–10 min;
(ii) 19, C$_5$H$_5$N, CH$_2$Cl$_2$, −40° C., 15 min, b, C$_5$H$_5$N—H$_2$O (1:1 v/v), −40° C. to room temp.
(iii) 4 M HCl/dioxane, CH$_2$Cl$_2$, −50° C., 5 min;
(iv) Ac$_2$O, C$_5$H$_5$N, room temp., 15 h;
(v) 20, TMG, MeCN, room temp., 12 h;
(vi) a, conc. aq. NH$_3$ (d 0.88), 50° C., 15 h, b, Amberlite IR-120 (plus), Na+ form, H$_2$O;
(vii) a, 21, C$_5$H$_5$N, CH$_2$Cl$_2$, −40° C., 15 min, b, C$_5$H$_5$N—H$_2$O (1:1 v/v), −40° C. to room temp.;
(viii) DBU, Me$_3$SiCl, CH$_2$Cl$_2$, room temp., 30 min;
(ix) 20, DBU, MeCN, room temp., 12 h.

From Scheme 2, the synthesis of oligonucleotides proceeds through intermediates 8, 9, 10 and 11 and the preparation of the phosphorothioate analogues proceeds through intermediates 8, 9, 12 and 13. Bases 14, 15 and 16 correspond to protected adenine, protected cytosine and protected guanine. Base 17 corresponds to thymine which does not require protection. Any conventionally used protecting group can be used. In the synthesis of RNA, thymine will be replaced by uracil. Compound 18 is a suitable coupling agent, and compounds 19 and 21 are suitable sulfur transfer agents. These compounds are referred to more fully hereinbelow.

The monomeric building blocks required in the coupling procedure according to the invention illustrated in Scheme 2 are triethylammonium 5'-O-(4-4'-dimethoxytrityl)-2'-deoxyribonucleoside 3'-H-phosphonates 8 (Bases B and B'=14–17) which can readily be prepared in almost quantitative yields from the corresponding protected nucleoside derivatives by a recently reported procedure (Ozola, V., Reese, C. B., Song Q. Tetrahedron Lett., 1996, 37, 8621–8624). By way of illustration, triethylammonium 5'-O-(dimethoxytrityl)-2'-deoxyribonucleoside 3'-H-phosphonates 8 were prepared as follows: Ammonium 4-methylphenyl H-phosphonate 30 (2.84 g, 15.0 mmol), 5'-O-(dimethyoxytrityl)-2'-deoxyribonucleoside derivative (5.0 mmol), triethylamine (4.2 ml, 30 mmol) and dry pyridine (20 ml) were evaporated together under reduced pressure. The residue was coevaporated again with dry pyridine (20 ml). The residue was dissolved in dry pyridine (40 ml) and the solution was cooled to −35° C. (industrial methylated spirits/dry ice bath). Pivaloyl chloride (1.85 ml, 15.0 mmol) was added dropwise to the stirred solution over a period of 1 min, and the reactants were maintained at −35° C. After 30 min, water (5 ml) was added, and the stirred mixture was allowed to warm up to room temperature. Potassium phosphate buffer (1.0 mol dm$^{-3}$, pH 7.0, 250 ml) was added to the products, and the resulting mixture was concentrated under reduced pressure until all of the pyridine had been removed. The residual mixture was partitioned between dichloromethane (250 ml) and water (200 ml). The organic layer was washed with triethylammonium phosphate buffer (0.5 mol dm$^{-3}$, pH 7.0, 3×50 ml), dried (MgSO$_4$)and then evaporated under reduced pressure. The reside was fractionated by short column chromatography on silica gel (25 g). Appropriate fractions, eluted with dichloromethane-methanol (95:5 to 90:10 v/v), were evaporated to give (5'-O-(dimethoxytrityl)-2'-deoxyribonucleoside 3'-H-phosphonate 8.

When triethylammonium 6-N-benzoyl-5'-O-(4,4'-dimethoxytrityl)-2'-deooxyadenosine 3'-H-phosphonate (DMTr-Ap(H))(Ozola et al., Tetrahedron, 1996), 8 (B=14), 4-N-benzoyl-3'-O-levulinoyl-2'-deoxycytidine (HO-C-Lev) 9 (B'=15) and di-(2-chlorophenyl)phosphorochloridate 18 were allowed to react together in pyridine -dichloromethane solution at −40° C., the corresponding fully-protected dinucleoside H-phosphonate (DMTr-Ap(H)C-Lev) was obtained apparently in quantitative yield within 5–10 minutes. The protocol used in this particular example was the dropwise addition of a solution of di-(2-chlorophenyl) phosphorochloridate (2.03 g, 6.0 mmol) in dichloromethane (4 ml) over 5 min to a stirred, dry solution of the triethylammonium salt of DMTr-Ap(H) 8 (B=14) (3.95 g, ca., 4.8 mmol) and 4-N-benzoyl-3'-O-levulinoyl-2'-deoxycytidine 9 (B'=15) (1.72 g, 4.0 mmol) in pyridine (36 ml), maintained at -40° C (industrial methylated spirits+dry ice bath). After a further period of 5 min, only one nucleotide product, assumed to be DMTr-Ap(H)C-Lev, and some remaining H-phosphonate monomer 8 (B=14) could be detected by reverse phase HPLC). However, it should be noted that these reaction conditions can be varied appropriately.

It is particularly noteworthy that such a high coupling efficiency was achieved with only ca. 20% excess of H-phosphonate monomer. No attempt was made to isolate the intermediate dinucleoside H-phosphonate (DMTr-Ap(H) C-Lev).

N-[(4-Chlorophenyl)sulfanyl]phthalimide 19 (2.32 g, 8.0 mmol) (Behforouz, M.; Kerwood, J. E. *J. Org. Chem,* 1969, 34, 51–55) was added to the stirred reactants which were maintained at −40° C. After 15 min, the products were worked up and chromatographed on silica gel and the corresponding S-(4-chlorophenyl) dinucleoside phosphorothioate DMTr-Ap(s')C-Lev 10 (B=14, B'=15) was obtained in ca. 99% isolated yield. Thus both coupling and the sulfur-transfer steps proceeded relatively quickly and virtually quantitatively at −40° C.

The four step procedure (Scheme 2, steps iii–vi) for the unblocking of DMTr-Ap(s')C-Lev 10 (B=14, B'=15) preferably involves 'detritylation', acetylation of the 5'-terminal hydroxy function, oximate treatment, and finally treatment with concentrated aqueous ammonia to remove acyl protecting groups from the base residues and from the 3'- and 5'-terminal hydroxy functions. In this way, extremely pure d[ApC] 11 (B=adenin-9-yl, B'=cytosine-1-yl) was obtained without further purification and isolated as its sodium salt. The monomeric building blocks 8 (B=17) and 9 (B'=16) were coupled together in the same way and on the same scale. After sulfur transfer with N-[(4-chlorophenyl) sulfanyl]phthalimide 19, the fully protected dinucleoside phosphorothioate DMTr-Tp(s')G-Lev 10 (B=17, B'=16) was isolated in ca. 98% yield. Again, very pure d[TpG] 11 (B=thymin-1-yl, B'=guanin-9-yl) was obtained when this material was unblocked by the above procedure (Scheme 2, steps iii–vi).

The protocol for the preparation of fully-protected oligonucleotide phosphorothioates differs from that used for oligonucleotide synthesis only in that sulfur-transfer is effected with 4-[(2-cyanoethyl)sulfanyl]morpholine-3,5-dione 21 or 3-(phthalimidosulfanyl)propanonitrile. However, 4-[(2-cyanoethyl)sulfanyl]morpholine-3,5-dione has the advantage that the morpholine-3,5-dione produced in the course of sulfur-transfer is more water-soluble than phthalimide. Triethylammonium 6-O-(2,5-dichlorophenyl)-5'-O-(4,4'-dimethoxytrityl)-2-N-isobutyryl-2'-deoxyguanosine 3'-H-phosphonate (DMTr-Gp(H)) 8 (B=16) [ca. 4.8 mmol], 6-N-benzoyl-3'-Olevulinoyl-2'-deoxyadenosine (HO-A-Lev) 9 (B=14) [4.0 mmol] and di-(2-chlorophenyl)phosphorochloridate 18 [6.0 mmol] were allowed to react together in pyridine—dichloromethane solution at −40° C. for 5–10 minutes 4-[(2-Cyanoethyl)sulfanyl]morpholine-3,5-dione 21 [8.0 mmol] (Scheme 2, step vii) was then added while the reactants were maintained at −40° C. After 15 minutes, the products were worked up and fractionated by chromatography on silica gel to give the fully-protected dinucleoside phosphorothioate (DMTr-Gp(s)A-Lev) 12 (B=14, B'=16) in 99% isolated yield. This material was unblocked by a five-step procedure (Scheme 2, steps iii, iv, viii, ix and vi). Following the 'detritylation' and acetylation steps, the product was treated with 1,8-diazabicyclo[5.4.0]undec-7-ene (DBU) under strictly anhydrous conditions to remove the S-(2-cyanoethyl) protecting group. The 6-O-(2,5-dichlorophenyl) protecting group was then removed from the guanine residue by oximate treatment, and finally all of the acyl protecting groups were removed by ammonolysis. The oximate treatment step can be omitted if the oligonucleotide phosphorothioate does not contain any 2'-deoxyguanosine residues. Extremely pure d[Gp(s)A] 13 (B=guanin-9-yl, B'=adenin-9-yl) was obtained without further purification, and was isolated as its sodium salt.

Preparation of 4-[(2-cyanoethyl)sulfanyl] morpholine-3,5-dione

S-(2-cyanoethyl)isothiouronium chloride was prepared as follows. Thiourea (304 g), was dissolved with heating in concentrated hydrochloric acid (500 ml). The resulting solution was evaporated under reduced pressure and the residual colourless solid was dissolved in boiling absolute ethanol (1300 ml). The solution was cooled to room temperature and acrylonitrile (400 cm$^3$) was added in portions with stirring. The reactants were heated, under reflux, for 2 hours. The cooled products were filtered and the residue was washed with cold ethanol and then dried in vacuo over calcium chloride.

Di-(2-cyanoethyl)disulphide was then prepared as follows. Dichloromethane (400 ml) was added to a stirred solution of S-(2-cyanoethyl)isothiouronium chloride (83.0 g) in water (500 ml) at 0° C. (ice-water bath). Sodium perborate tetrahydrate (44.1 g) was added, and then a solution of sodium hydroxide (30.0 g) in water (250 ml) was added dropwise. The reactants were maintained at 0° C. (ice-water bath). After 5 hours, the products were separated and the aqueous layer was extracted with dichloromethane (3×50 ml). The combined organic layers were dried ($MgSO_4$) and evaporated under reduced pressure to give a solid which was recrystallised from methanol (30 ml) to give colourless crystals.

Di-(2-cyanoethyl)disulphide (4.51 g) and morpholin-2,6-dione (5.75 g) were suspended in acetonitrile (10 ml), dichloromethane (20 ml) and 2,6-lutidine (17.4 ml) and cooled to 0° C. (ice-water bath). A solution of bromine (4.28 g) in dichiomethane (20 ml) was added over 30 minutes. The reaction mixture was allowed to stir at 0° C. for 1.5 hours. The product was then precipitated by the addition of ice-cold methanol (50 ml) over 30 minutes and filtered to give the title compound (8.23 g, 82%). Recrystallisation from ethyl acetate gave 4-[(2-cyanoethyl)sulfanyl]morpholine-3,5-dione as colourless needles, m.p. 121–122° C.

Reaction Scheme for Preparation of Chimeric Oligonucleotides

The stepwise synthesis of d[TpGp(s)ApC] 25 which has one phosphorothioate diester and two phosphodiester internucleotide linkages is illustrated in outline by way of example in Scheme 3.

Scheme 3

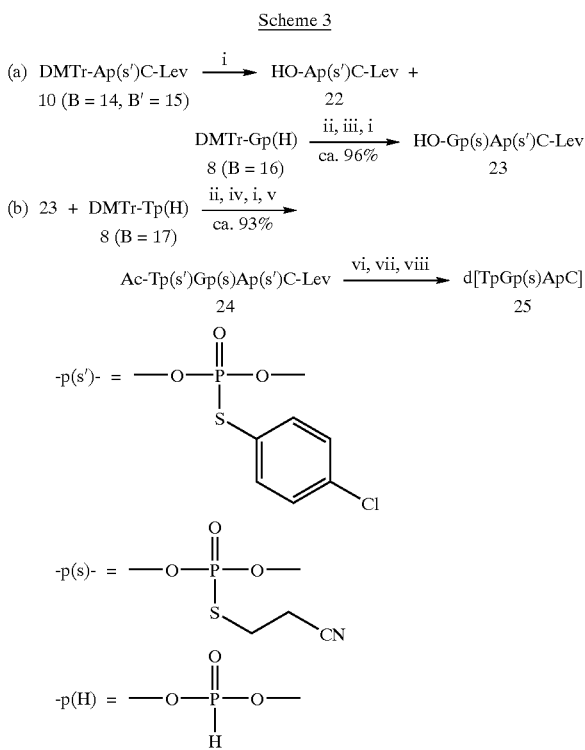

Reagents and conditions:

(i) 4 M HCl/dioxane, CH$_2$Cl$_2$, −50° C., 5 min;

(ii) 18, C$_5$H$_5$N, CH$_2$Cl$_2$, −40° C., 5–10 min;

(iii) a, 21, C$_5$H$_5$N, CH$_2$Cl$_2$, −40° C., 15 min, b, C$_5$H$_5$N—H$_2$O (1:1 v/v), −40° C. to room temp;

(iv) a, 19, C$_5$H$_5$N, CH$_2$Cl$_2$, −40° C., 15 min, b, C$_5$H$_5$N—H$_2$O (1:1 v/v), −40° C. to room temp;

(v) Ac$_2$O, C$_5$H$_5$N, room temp., 15 h;

(vi) DBU, Me$_3$SiCl, CH$_2$Cl$_2$, room temp., 30 min;

(vii) 20, DBU, MeCN, room temp., 12 h; (viii) a, conc. aq. NH$_3$(d 0.88), 50° C., 15 h, b, Amberlite IR-120 (plus), Na+form, H$_2$O.

No limitation of scale is anticipated. The reactions shown in Scheme 3 are not intended to be limiting and the method of the invention is equally suitable for the synthesis of RNA, 2'-O-alkyl-RNA and other oligonucleotide sequences.

All of the reactions involved were used above either in the preparation of d[ApC] 11 (B=adenin-9-yl, B'=cytosin-1-yl or of d[Gp(s)A] 13 (B=guanin-9-yl, B'=adenin-9-yl) (Scheme 2).

First, the fully-protected dinucleoside phosphorothioate DMTr-Ap(s')C-Lev 10 (B=14, B'=15) [ca. 0.75 mmol] was converted in four steps and in ca. 96% overall isolated yield (Scheme 3a) into the partially-protected trimer 23. In each coupling step, a ca. 20% excess of H-phosphonate monomer 8 was used, but the excess of coupling agent 18 depended on the scale of the reaction. In addition, a twofold excess of sulfur-transfer agent 19 or 21 was used in this example. The products were chromatographed on silica gel after each "detritylation" step.

This material was then coupled with DMTr-Tp(H) 8 (B=17) and the product was converted in three steps and in ca. 93% overall yield (Scheme 3b) into the fully-protected tetramer 24. The latter material was unblocked to give d[TpGp(s)ApC] 25 which was isolated without further purification as its relatively pure (ca. 96.5% by HPLC) sodium salt.

The tetranucleoside triphosphate d[TpGpApC] and the tetranucleoside triphosphorothioate d[Cp(s)Tp(s)Gp(s)A] were also prepared by stepwise synthesis in very much the same way. The protocols followed differed from that outlined in Scheme 3 only stepwise synthesis in very much the same way. The protocols followed differed from that outlined in Scheme 3 only inasmuch as the sulfur-transfer agent 19 was used exclusively in the preparation of d[TpGpApC] and the sulfur-transfer agent 21 was used exclusively in the preparation of d[Cp(s)Tp(s)Gp(s)A].

Reaction Scheme for Block Coupling

By way of illustration, Scheme 4 given herein-below illustrates an example of block coupling which is part of the invention.

Scheme 4

(a) Ac-Tp(s)Tp(s)Gp(s)G-Lev $\xrightarrow{\text{i, ii}}$ Ac-Tp(s)Tp(s)Gp(s)Gp(H)
26                                       27

(b) Ac-Tp(s)Tp(s)Gp(s)Gp(H) + HO-Gp(s)Gp(s)Tp(s)T-Bz $\xrightarrow{\text{iii, iv}}$
          27                     28

Ac-Tp(s)Tp(s)Gp(s)Gp(s)Gp(s)Gp(s)Tp(s)T-Bz
29

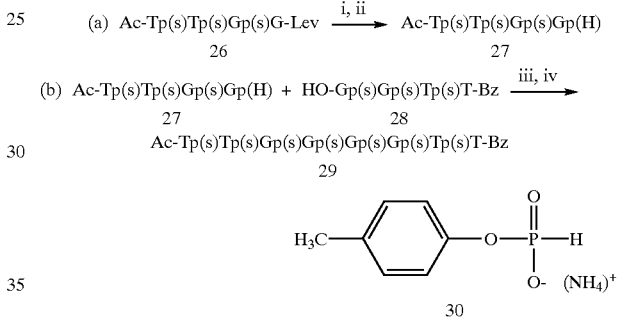

30

Reagents and conditions:

(i) N$_2$H$_4$·H$_2$O, C$_5$H$_5$N—AcOH (3:1 v/v), 0° C., 20 min;

(ii) a, 30, Me$_3$C—COCl, C$_5$H$_5$N, −35° C., 30 min, b, Et$_3$N, H$_2$O;

(iii) 18 C$_5$H$_5$N, CH$_2$Cl$_2$, −35° C.; (iv) a, 21, C$_5$H$_5$N, CH$_2$Cl$_2$, −35° C., 10 min, b, C$_5$H$_5$N—H$_2$O (1:1 v/v), −35° C. to room temp.

The fully protected octadeoxynucleoside heptaphosphorothioate 29 which was obtained in 91% isolated yield is a precursor of d[Tp(s)Tp(s)Gp(s)Gp(s)Gp(s)Gp(s)Tp(s)T]. As indicated above, block coupling is much more feasible in solution than in solid phase synthesis.

This approach is of course not in any way limited to tetramer coupling. Indeed, it is anticipated that this H-phosphonate approach will be suitable for coupling quite large oligonucleotide blocks (for example, 10+10) together.

Reaction Scheme for Preparation of Block H-phosphonates

For example, partially-protected oligonucleotides 33a and the corresponding phosphorothioates 33b which can be prepared by the conventional phosphotriester approved in solution (Chattopadhyaya, J. B.; Reese, C. B. *Nucleic Acids Res.*, 1980, 8, 2039–2054; Kemal, O., Reese, C. B.; Serafinowska, H. T. *J. Chem. Soc., Chem. Commun.*, 1983, 591–593) can similarly be converted into their 3'-H-phosphonates (34a and 34b, respectively) as indicated in Scheme 5.

Scheme 5

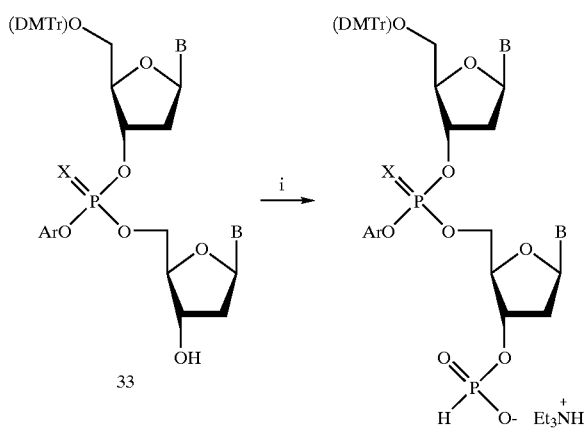

a, X = O, Ar = 2-ClC$_6$H$_4$; b, X = S, Ar = 2,5-Cl$_2$C$_6$H$_3$.

Reagents and conditions:
(i) a, 30, Me$_3$C.COCl, C$_5$H$_5$N, −35° C., b, Et$_3$N, H$_2$O.

Example 1

Ac-Tp(s)Tp(s)Gp(s)G-OH

HO-Tp(s)Tp(s)Gp(s)G-Lev (5.82 g, 3 mmol) was co-evaporated with anhydrous pyridine (2×20 ml) and redissolved in anhydrous pyridine (30 ml). Acetic anhydride (1.42 ml, 15 mmol) was added and the reaction solution was allowed to stir at room temperature for 12 h. Water (1.5 ml) was added to quench the reaction. After 10 min, the mixture was cooled to 0° C. (ice-water bath) and hydrazine hydrate (1.50 g, 30 mmol) in pyridine (15 ml) and glacial acetic acid (15 ml) was added. The mixture was stirred at 0° C. for 20 min and was then partitioned between water (100 ml) and CH$_2$Cl$_2$ (100 ml). The two layers were separated and the organic layer was washed with water (3×50 ml). The organic layer was dried (MgSO$_4$) and evaporated. The residue was purified by silica gel chromatography. Impurities were eluted with methanol-dichloromethane (4:96 v/v) the main product was eluted with acetone. Evaporation of the appropriate fractions gave the partially protected tetradeoxynucleoside triphosphorothioate as colourless solid (5.30 g, 93%).

Example 2

Ac-Tp(s)Tp(s)Gp(s)Gp(H)

The ammonium salt of 4-methylphenyl H-phosphonate (1.42 g, 7.5 mmol) was dissolved in the mixture of methanol (15 ml) and triethylamine (2.1 ml, 15 mmol). The mixture was evaporated and coevaporated with pyridine (2×10 ml) under reduced pressure. Ac-Tp(s)Tp(s)Gp(s)G-OH (4.71 g, 2.5 mmol) was added and co-evaporated with dry pyridine (20 ml). The residue was dissolved in dry pyridine (20 ml) and pivaloyl chloride (1.23 ml, 10 mmol) was added at −35° C. in 1 min. After 30 min at the same temperature, water (5 ml) was added and the mixture was allowed to warm to room temperature and stir for 1 hr. The solution was partitioned between water (100 ml) and dichloromethane (100 ml). The organic layer was separated and washed with triethylammonium phosphate buffer (pH 7.0, 0.5M, 3×50 ml), dried (MgSO$_4$), and then filtered and applied to a silica gel column (ca. 25 g). The appropriate fractions, which were eluted with methanol-dichloromethane (20:80, v/v), were evaporated to give Ac-Tp(s)Tp(s)Gp(s)Gp(H), as a colourless solid (4.85 g, 94%).

Example 3

Ac-Tp(s)Tp(s)Gp(s)Gp(s)Gp(s)Gp(s)Tp(s)T-Bz

Ac-Tp(s)Tp(s)Gp(s)Gp(H) (1.229 g, 0.6 mmol) and HO-Gp(s)Gp(s)Tp(s)T-Bz (0.973 g, 0.5 mmol) were coevaporated with anhydrous pyridine (2×10 ml) and the residue was dissolved in anhydrous pyridine (10 ml). The solution was cooled to −35° C. (Industrial methylated spirits-dry ice bath) and di-(2-chlorophenyl) phosphorochloridate (0.84 g, 2.5 mmol) in dry dichloromethane (1 ml) was added over 10 min. 4-[(2-Cyanoethyl)sulfanyl]morpholin-3,5-dione (0.20 g, 1.0 mmol) was added and the mixture was allowed to stir for 10 min at the same temperature. Then water-pyridine (0.2 ml, 1:1 v/v) was added and the mixture was stirred for a further 5 min. The reaction mixture was then evaporated under reduced pressure. The residue was dissolved in dichloromethane (100 ml) and the solution was washed with saturated aqueous sodium bicarbonate solution (3×50 ml). The organic layer was dried (MgSO$_4$) and concentrated under reduced pressure. The residue was purified by silica gel chromatography. Firstly, the lipophilic impurities were removed with methanol-dichloromethane (4:96 v/v), and then the main product was eluted with acetone. Evaporation of the appropriate fractions gave fully protected octadeoxynucleoside heptaphosphorothioate as colourless solid (1.81 g, 91%). The fully-protected octadeoxynucleoside heptaphosphorothioate which was obtained in 91% isolated yield is a precursor of d[Tp(s)Tp(s)Gp(s)Gp(s)GpO(s)Gp(s)Tp(s)T].

What is claimed is:

1. A process for the preparation of a phosphorothioate triester which comprises the solution phase coupling of an H-phosphonate with an alcohol in the presence of a coupling agent thereby to form an H-phosphonate diester and, in situ, reacting the H-phosphonate diester with a sulfur transfer agent to produce a phosphorothioate triester.

2. A process according to claim 1 wherein the H-phosphonate is a protected nucleoside or oligonucleotide comprising a 3'-H-phosphonate function.

3. A process according to either of claims 1 and 2, wherein the alcohol is a protected nucleoside or oligonucleotide comprising a free 5'-hydroxy function.

4. A process according to claim 1, wherein the coupling agent is a diaryl phosphorochloridate of formula (ArO)$_2$POCl, in which Ar represents phenyl, 2-chlorophenyl, 2,4,6-trichlorophenyl or 2,4,6-tribromophenyl.

5. A process according to claim 1, wherein the sulfur transfer agent has the general chemical formula:

L—S—A wherein L represents a leaving group, and A represents an aryl group, a methyl group, a substituted alkyl group or an alkenyl group.

6. A process according to claim 5, wherein the leaving group is a morpholine-3,5-dione, phthalimide, succinimide, maleimide or indazole, and A represents a 4-halophenyl group, 4-alkylphenyl group, methyl group, benzyl group, alkylbenzyl group, halobenzyl group, allyl group, crotyl group, 2-cyanoethyl group or a 2-(4-nitrophenyl)ethyl group.

7. A process according to claim 1, wherein the H-phosphonate and the alcohol are selected from the group consisting of deoxyribonucleosides, oligodeoxyribonucleotides, ribonucleosides, 2'-O-(alkyl, alkoxyalkyl or alkenyl)-ribonucleosides, oligoribonucleotides and 2'-O-alkyl, alkoxyalkyl or alkenyl)-oligoribonucleotides.

8. An H-phosphonate having the general chemical formula:

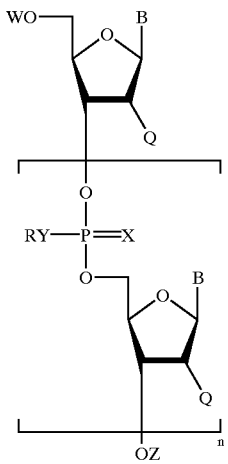

wherein
each B independently is a base selected from A, G, T, C or U;
each Q independently is H or OR' wherein R' is alkyl, substituted alkyl, alkenyl or a protecting group;
each R independently is an aryl, methyl, substituted alkyl or alkenyl group;
W is H, a protecting group or an H-phosphonate group of formula

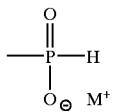

in which
$M^+$ is a monovalent cation;
each X independently represent O or S;
each Y represents S;
Z is H, a protecting group or an H-phosphonate group of formula

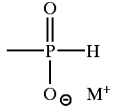

in which
$M^+$ is a monovalent cation; and
n is an integer;
provided that when W is H or a protecting group, that Z is a positive H-phosphonate group, and that when Z is H or a protecting group, that W is an H-phosphonate group.

9. An H-phosphonate according to claim 6, wherein W represents a protecting group, each X represents O, and each R represents a methyl group, a benzyl group, a 2-cyanoethyl group, an unsubstituted phenyl group or a 4-halophenyl group, M+ represents a tri($C_{1-4}$-alkylammonium) ion, and n is 1 to 16.

10. An H-phosphonate according to either of claim 9 or 10, wherein n is 1, 2 or 3.

11. A process according to claim 1, wherein the coupling agent is a diaryl phosphorochloridate of formula (ArO)$_2$POCl, in which Ar represents phenyl, 2-chlorophenyl, 2,4,6-trichlorophenyl or 2,4,6-tribromophenyl; and the sulfur transfer agent has the general chemical formula:

wherein L represents a leaving group, and A represents an aryl group, a methyl group, a substituted alkyl group or an alkenyl group.

12. A process according to claim 11, wherein the leaving group is a morpholine-3,5-dione, phthalimide, succinimide, maleimide or indazole, and A represents a 4-halophenyl group, 4-alkylphenyl group, methyl group, benzyl group, alkylbenzyl group, halobenzyl group, allyl group, crotyl group, 2-cyanoethyl group or a 2-(4-nitrophenyl)ethyl group.

13. A process according to claim 11 or 12, wherein the H-phosphonate and the alcohol are each independently a deoxyribonucleoside, an oligodeoxyribonucleotide, a ribonucleoside, a 2'-O-(alkyl, alkoxyalkyl or alkenyl)-ribonucleoside, an oligoribonucleotide or a 2'-O-(alkyl, alkoxyalkyl or alkenyl)-oligoribonucleotide.

14. A process for the preparation of a deprotected phosphodiester oligonucleotide, deprotected phosphorothioate oligonucleotide or a deprotected oligonucleotide comprising both phosphodiester and phosphorothioate diester internucleotide linkages which comprises:

(a) solution phase coupling of a protected nucleoside or oligonucleotide H-phosphonate comprising a 3' or 5'-H-phosphonate function with a protected nucleoside or oligonucleotide comprising a free 3' or 5'-hydroxy function in the presence of a coupling agent thereby to form an H-phosphonate diester and, in situ, reacting the H-phosphonate diester with a sulfur transfer agent to produce a phosphorothioate triester; and (b) deprotecting the phosphorothioate triester produced in (a) thereby to form a deprotected phosphodiester oligonucleotide, deprotected phosphorothioate oligonucleotide or a deprotected oligonucleotide comprising both phosphodiester and phosphorothioate diester internucleotide linkages.

15. A process according to claim 14, wherein the protected nucleoside or oligonucleotide H-phosphonate comprises a 3' H-phosphonate function and the protected nucleoside or oligonucleotide comprises a free 5'-hydroxy function.

16. A process according to claim 14 or 15, wherein the coupling agent is a diaryl phosphorochloridate of formula (ArO)$_2$POCl, in which Ar represents phenyl, 2-chlorophenyl, 2,4,6-trichlorophenyl or 2,4,6-tribromophenyl.

17. A process according to claim 14 or 15, wherein the sulfur transfer agent has the general chemical formula:

wherein L represents a leaving group, and A represents an aryl group, a methyl group, substituted alkyl group or an alkenyl group.

18. A process according to claim 17, wherein the leaving group is a morpholine-3,5-dione, phthalimide, succinimide, maleimide or indazole, and A represents a 4-halophenyl group, 4-alkylphenyl group, methyl group, benzyl group, alkylbenzyl group, halobenzyl group, allyl group, crotyl group, 2-cyanoethyl group or a 2-(4-nitrophenyl)ethyl group.

19. A process according to claim 14 or 15, wherein an oligonucleotide H-phosphonate and/or an oligonucleotide comprising a free 3' or 5'-hydroxy function is employed and either or both of the oligonucleotide H-phosphonate and the oligonucleotide comprising a free 3' or 5'-hydroxy function comprise one or more phosphorothioate internucleotide linkages.

20. A process according to claim 14 or 15, wherein the deprotected phosphodiester oligonucleotide, deprotected phosphorothioate oligonucleotide or a deprotected oligonucleotide comprising both phosphodiester and phosphorothioate diester internucleotide linkages is subsequently purified.

21. A process according to claim 20, wherein a deprotected phosphorothioate oligonucleotide is produced.

22. A process according to claim 2, wherein the H-phosphonate comprising a 3' H-phosphonate function is a protected oligonucleotide H-phosphonate comprising at least one phosphorothioate internucleotide linkage.

23. A process according to claim 3, wherein the alcohol comprising a free 5'-hydroxy function is an oligonucleotide comprising a, least one phosphorothioate internucleotide linkage.

24. A process according to claim 23, wherein the H-phosphonate is a protected oligonucleotide H-phosphonate comprising a 3' H-phosphonate function and also comprises at least one phosphorothioate internucleotide linkage.

* * * * *

UNITED STATES PATENT AND TRADEMARK OFFICE
CERTIFICATE OF CORRECTION

PATENT NO. : 6,506,894 B1
DATED : January 14, 2003
INVENTOR(S) : Reese et al.

It is certified that error appears in the above-identified patent and that said Letters Patent is hereby corrected as shown below:

Column 7,
Lines 38-39, please delete "approximately—55ºC" and insert -- approximately -55ºC --;

Column 10,
Line 14, please delete "at—50ºC" and insert -- at -50ºC --;

Column 25,
Line 4, please delete "2'-O-alkyl," and insert -- 2'-O-(alkyl, --;
Line 60, please delete "an" and insert -- a positive --;
Line 62, please delete "positive";
Line 65, please delete "claim 6" and insert -- claim 8 --;

Column 26,
Lines 4-5, please delete "claim 9 or 10" and insert -- claim 8 or 9 --; and Column 28,
Line 9, please delete "a," and insert -- at --.

Signed and Sealed this

Twenty-ninth Day of July, 2003

JAMES E. ROGAN
*Director of the United States Patent and Trademark Office*